United States Patent [19]

Bachalo

[11] Patent Number: 4,540,283
[45] Date of Patent: Sep. 10, 1985

[54] APPARATUS AND METHOD FOR DETERMINING THE SIZE AND VELOCITY OF PARTICLES, DROPLETS, BUBBLES OR THE LIKE USING LASER LIGHT SCATTERING

[76] Inventor: William D. Bachalo, 14660 Saltamontes Way, Los Altos Hills, Calif. 94022

[21] Appl. No.: 506,108

[22] Filed: Jun. 20, 1983

[51] Int. Cl.³ .............................................. G01N 15/02
[52] U.S. Cl. .................................... 356/336; 356/28.5; 356/343
[58] Field of Search ............... 356/336, 338, 343, 28.5

[56] References Cited

U.S. PATENT DOCUMENTS 4,329,054  5/1982  Bachalo ............................... 356/336
4,387,993  6/1983  Adrian ................................. 356/336

OTHER PUBLICATIONS

Farmer, "Measurement of Particle Size, Number Density, and Velocity Using a Laser Interferometer", *Applied Optics*, vol. 11, No. 11, pp. 2603–2612, 11/72.
Holz et al., "Tracking Bacterial Movements Using a One-Dimensional Fringe System", *Optics Letters*, vol. 2, No. 5, pp. 109–111, 5/78.
Bachalo, "Method for Measuring the Size and Velocity of Spheres by Dual-Beam Light-Scatter Interferometry", *Applied Optics*, vol. 19, No. 3, pp. 363–367, 2/80.

*Primary Examiner*—Davis L. Willis
*Assistant Examiner*—Matthew W. Koren
*Attorney, Agent, or Firm*—Jeffrey J. Blatt

[57] ABSTRACT

An apparatus and method for determining the size and velocity of particles, droplets, bubbles, or the like employing laser light scattering is disclosed. A laser generation means is provided for generating a pair of coherent laser beams. These beams are directed along an axis and are caused to cross the axis at an angle to establish a sample volume. A collection means for sensing the scattering caused by particles, droplets, bubbles or the like within the sample volume is provided. The collected scattered signals are directed onto photo-detectors which are coupled to a signal phase determining means for determining the phase of the scattered signals as the particle, droplet, bubble or the like passes through the sample volume. Sizing means are coupled to the signal phase determining means for determining the size of the particle, droplet, bubble or the like from phase changes and the scattered signal. The velocity of the particle, droplet, bubble or the like is determined using well known laser Doppler anemometry techniques. In addition, the present invention discloses a method to determine the direction of motion of a particle, droplet, bubble or the like passing through the sample volume.

26 Claims, 8 Drawing Figures

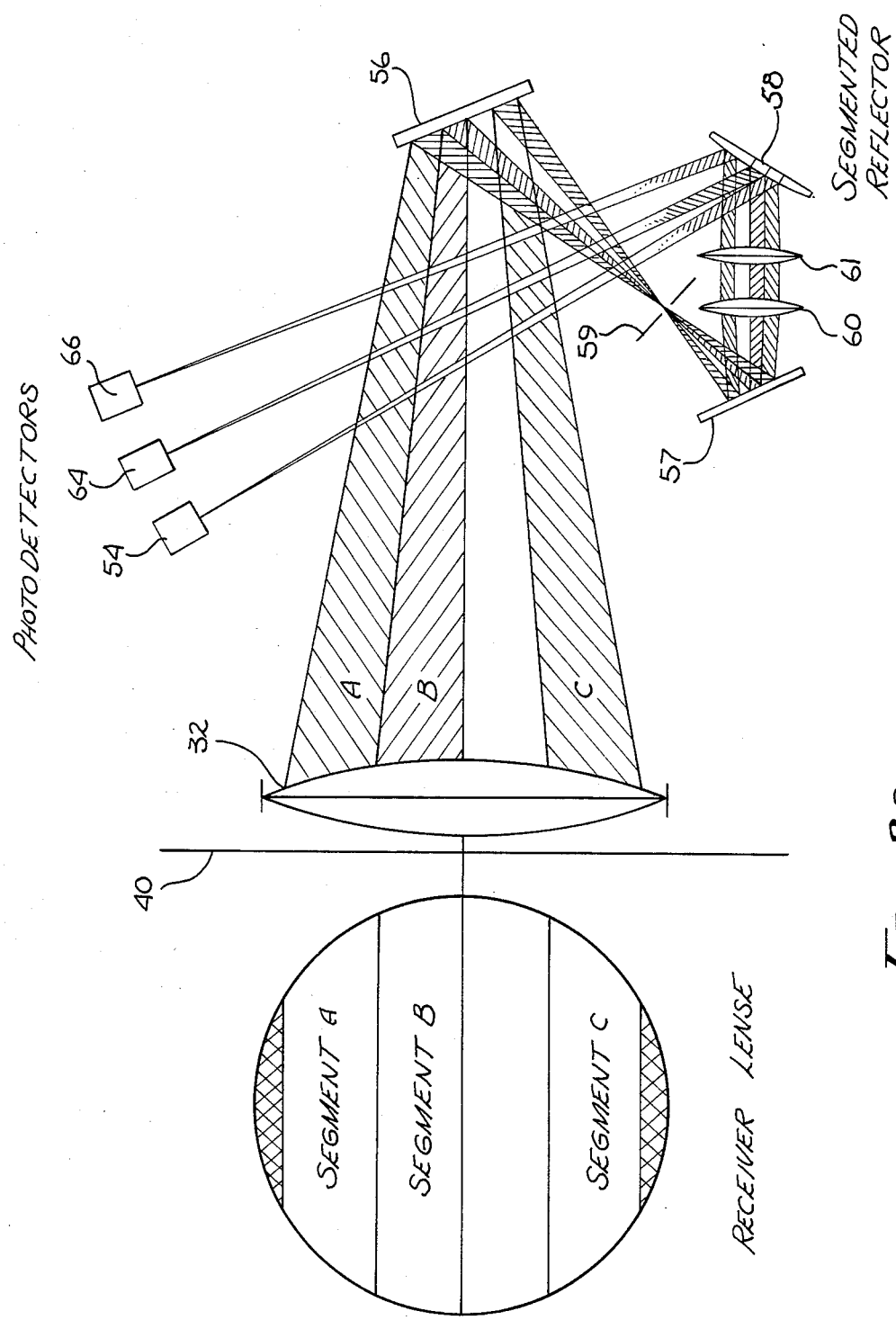

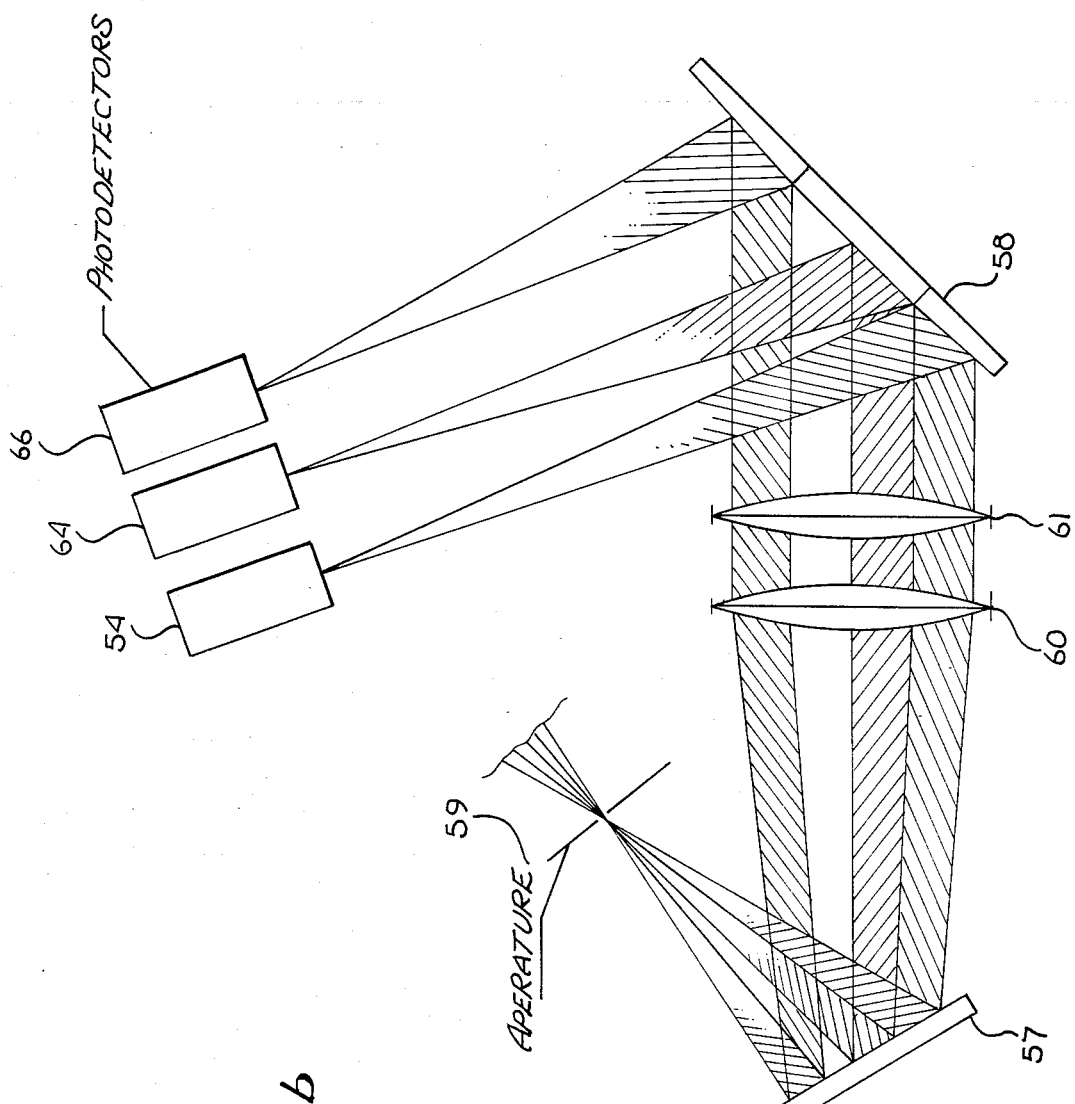

APPARATUS AND METHOD FOR DETERMINING THE SIZE AND VELOCITY OF PARTICLES, DROPLETS, BUBBLES OR THE LIKE USING LASER LIGHT SCATTERING

BACKGROUND OF THE INVENTION

1. Field

The present invention relates to the field of determining the parameters of particles, droplets, bubbles or the like, and more particularly, to the determination of particle size and velocity using laser light scattering.

2. Art Background

There has long been a need to measure particle, droplet, and bubble size in sprays, planetary atmospheres, combustion processes and the like. Such measurements are useful in aircraft icing studies, planetary studies, fuel analysis, and numerous combustion and nozzle applications. A number of techniques employing laser light scattering have been developed to determine the size and/or velocity of particles, droplets, bubbles or the like.

In one system, commonly referred to as a particle sizing interferometer, a pair of laser beams of equal size and intensity are caused to cross and form a sample volume. An interference pattern between the beams is established by this crossing, and particles passing through this volume scatter light in proportion to the spatially varying light intensity within the interference pattern. From the scattered light, information concerning both the particle's size and velocity can be computed. The particle size is determined from a visibility factor (V) which is a function of the relative maximum and minimum intensity of the received scattered signal. A more detailed explanation of this interferometric technique is given in by the inventor W. D. Bachalo in an article entitled "A Method For Measuring The Size and Velocity of Spheres By Dual Beam Scatter Interferometry", *Applied Optics*, Vol. 19, Feb. 1, 1980; and U.S. Pat. No. 4,329,054 which issued on May 11, 1982. However, the determination of particle size based on a visibility function may give rise to significant errors. Signal visibility used for determining a particle's size requires that complete interference of the laser light occur at the measurement volume. In order to accomplish this, the laser light source must have a high degree of coherence, the beams must be of equal intensity and polarization, and they must be exactly parallel and overlap identically at the beam cross-over defining the interference pattern. In addition, other droplets passing through the pattern may cause beam extinction during measurements of a particular particle's size and/or velocity. Moreover, prior art visibility based size measurements are generally limited to a size range of one decade or less.

An alternate approach to the visibility method was described by F. Durst and M. Zare, in a paper entitled "Laser Doppler Measurements in Two Phase Flows", *Proceedings of the LDA Symposium*, Copenhagen, 1975. In that work, it was recognized that the interference patterns reflected and refracted by particles, droplets, bubbles or the like could be related to the size of the particles. The Zurst model assumes that there are no fringes generated where the two laser beams cross, but rather, that the interference fringes are formed by scattered radiation from a particle, droplet or the like. The basic analysis provided by the authors illustrated that the shape and spacing of the fringes produced by reflection and refraction are functions of the angle between the incident laser beams, their wavelengths, as well as the direction of light collection and particle size. The authors derived formulas using a simple approach which are valid for small beam intersection angles, and large distance to observation and sphere size ratios. Although the authors claim that spherical particles could be measured using a double photo-detector apparatus, they later recognized that the size measurements required that the distance between the photo-detectors be matched to the fringe distance, and thus, to the particle size to be measured. They concluded that this requirement was a disadvantage for practical measurements of size distribution and rendered the method useful only for the measurement of size variations (e.g., the growth of a bubble). Moreover, the authors concluded that optical size measurements should be based on a direct recording of the fringe size using, for example, a vidicon tube, a multi-channel analyzer and a oscilloscope.

The proposed approach of Durst and Zare using a direct imaging means, such as a vidicon tube, encumbers the method with unnecessary information, slows the ultimate data rate of the system, and requires more extension software to extract the Doppler period and fringe spacing information. In addition, a further problem not acknowledged by Durst and Zare was the fact that their optical arrangement could not be used where the particle's trajectory is random as is the case of actual sprays. When the proposed photo-detectors are used without receiver lenses and apertures, scattered light from any point along the laser beam will reach the detector. However, in order to be functional, the two detectors must receive light simultaneously from only one spherical particle at a time.

As will be disclosed, the present invention provides apparatus and methods which permit particle sizing based on the phase variations of the scattered light caused by a particle, droplet, bubble or the like passing through an interference pattern. In addition, the present invention operates independently of the optical assumptions regarding the formation of interference fringes, and measures particles unambiguously over the wide range of sizes and number densities typical in spray and bubble environments.

SUMMARY OF THE INVENTION

An apparatus and method for determining the size and velocity of particles, droplets, bubbles or the like employing laser light scattering is disclosed. A laser generation means is provided for generating a pair of coherent laser beams. These beams are directed along an axis, and are caused to cross the axis at a given angle to establish an interference pattern and define a sample volume. A collection means for sensing the scattering caused by particles, droplets, bubbles or the like within the sample volume is provided. In the presently preferred embodiment, the collection means is situated off-axis by a predetermined angle from the axis defined by the two laser beams. The collected scattered signals are directed onto photo-detectors which are coupled to a signal phase determining means for determining the phase of the scattered signals as the particle, droplet, bubble or the like passes through the sample volume. Sizing means are coupled to the signal phase determining means for determining the size of the particle, droplet, bubble or the like from phase changes in the received scattered signals. The velocity of the particle, droplet, bubble or the like is determined using well-known laser Doppler anemometry techniques based on high frequency Doppler components in the received scattered signal.

BRIEF DESCRIPTION OF THE DRAWINGS

FIG. 2a illustrates the preferred collection means of the present invention which may be used in conjunction with the embodiment of FIG. 1.

FIG. 2b illustrates an enlarged view of the optical structure of FIG. 2a.

FIG. 4 diagrammatically illustrates the reflection and refraction of light rays through a droplet, bubble, or the like.

DETAILED DESCRIPTION OF THE INVENTION

An apparatus and method for determining the size and velocity of particles, droplets, bubbles or the like (hereinafter sometimes collectively referred to as "particles") using laser light scattering is disclosed. In the following description for purposes of explanation, numerous details are set forth such as specific wavelengths, angles, frequencies, etc., in order to provide a thorough understanding of the present invention. However, it will be apparent to one skilled in the art that the invention may be practiced without these specific details. In other instances, well known components, structures and electrical processing means have not been described in detail in order not to obscure the present invention unnecessarily.

Figure 1:
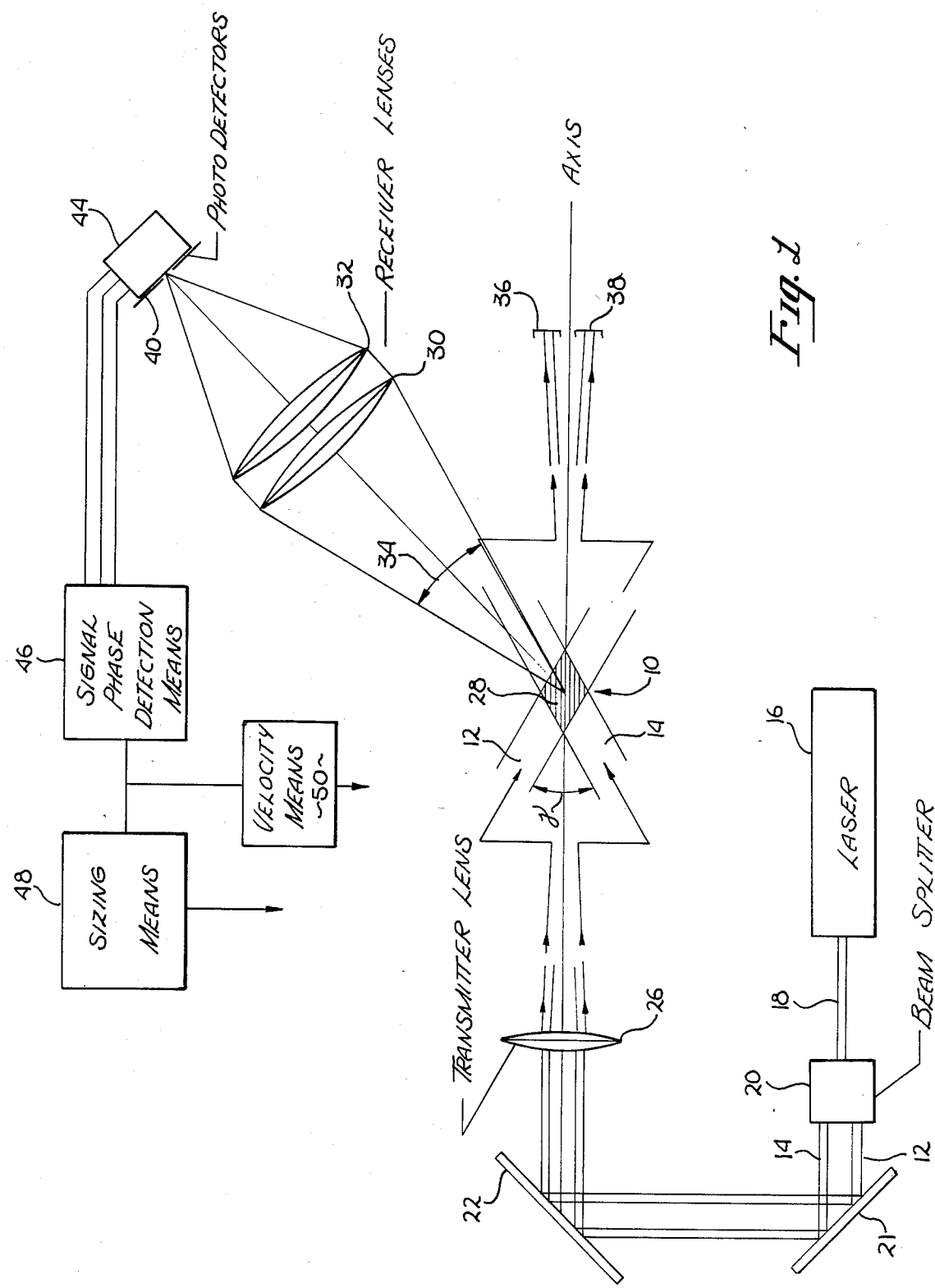
FIG. 1 is a diagrammatical representation of the presently preferred embodiment of the invention.

Referring now to FIG. 1, the apparatus for determining the size and velocity of particles, droplets, bubbles or the like includes a sample volume 10. The sample volume 10 is defined as the overlap region of a first laser beam 12 and a second laser beam 14, which are caused to cross at an angle gamma with respect to an axis defined through the intersection of the two beams.

The laser beams employed by the present invention are generated, in the presently preferred embodiment, by a single laser 16. The primary beam 18 generated by laser 16 is passed through a beam splitter 20 thereby forming the first and second laser beams 12 and 14, respectively. Beams 12 and 14 are reflected off of reflectors 21 and 22, and are passed through a focusing lens 26 which causes the beams to focus and cross at the desired angle and form sample volume 10. In the present embodiment, beams 12 and 14 are of the same wavelength and intensity.

The crossing of beams 12 and 14, as is well known, establishes the interference fringe pattern 28 within the sample volume 10. (Note that in FIG. 1, beams 12 and 14 have been broken and then shown in enlarged form within the sample volume 10 in order to illustrate the interference pattern 28). Particles, droplets, bubbles or the like passing through the sample volume 10 scatter light in proportion to the spatially varying light intensity of the fringe pattern. As will be discussed, the phase of the scattered light through this pattern carries information concerning a particle's size. The scattering is sensed by a collection means which includes lenses 30 and 32 which define a solid angle of collection 34 extending into the interference pattern 28. As shown, stops 36 and 38 terminate beams 12 and 14 downstream from the interference pattern 28.

The light scattered within the solid angle 34 by particles, droplets, bubbles or the like passing through the sample volume 10 is collected and focused by lenses 30 and 32 onto an aperture 40. Aperture 40 serves to admit only light scattered by particles crossing the laser beams in the appropriate portion of the sample volume 10. The collected scattered signal is, as will be discussed, focused onto photo-detectors 44 which are coupled to a signal phase detection means 46. Sizing means 48 is coupled to the signal phase detection means 46 for determining the size of particles, droplets, bubbles or the like passing through probe volume 10, as will be discussed, based on phase shifts within the collected signal. In addition, velocity means 50 is coupled to signal phase detection means 46 for determining the velocity of a particle, droplet, bubble or the like using well known laser Doppler anemometry principles.

Referring now to FIGS. 2a and 2b, the collection means of the present invention includes receiver lens 32 disposed beyond aperture 40, which focuses the collected scattered light energy (the "scattered signal") and serves to separate the signal into three segments. Thus, receiver lens 32 selectively separates collected scattered light energy from sample volume 10 into segments A, B and C as shown in FIG. 2a. That portion of the scattered signal falling within segment A is directed onto photo-detector 54 by the use of mirrors 56, 57, and 58, as well as aperture 59 and focusing lenses 60 and 61. It will be appreciated that although the illustrated embodiment utilizes a segmented reflecting mirror 58 to deflect light passing through segments A, B and C, that a variety of optical configurations may be used to accomplish this selective deflection. Similarly, that portion of the scattered signal falling within segments B and C is focused onto photo-detectors 64 and 66, respectively.

Thus, receiver lens 32 may be used to measure the spacing and movement of interference fringes as the particle, droplet or the like passes through sample volume 10. As the particle moves, the interference fringes sweep across the receiver lens 32. The output from photo-detectors 54, 64, and 66 is coupled to signal phase detection means 46. Signals from each of the photo-detectors are passed through linear and/or logrithmic preamplifiers (depending on the application). The preamplifiers serve to reduce the dynamic range of the signals to be processed by the phase detection means 46. Phase detection means 46 determines the phase angle between the signals from detectors 54, 64 and 66. These phase angles are converted to digital signals proportioned to the phase angles, using well-known circuitry.

The phase angles between the respective photo-detector outputs are determined by measuring the elaspsed time between corresponding "points" on the received signals (ex. between detectors 54 and 64 and between detectors 54 and 66). This elapsed time is then divided by the Doppler period to obtain the phase angle between the signals ($\phi = \tau_n / \tau_{Doppler}$). Moreover, a logic test is utilized in order to insure that the phase angles measured are for a single Doppler cycle.

Figure 3A:
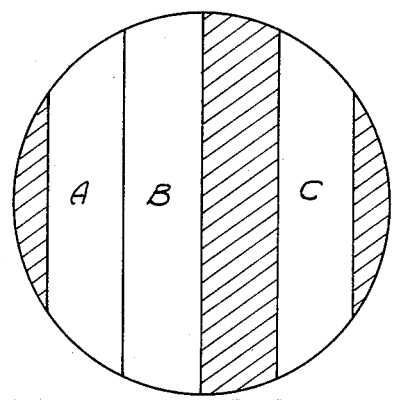
FIGS. 3a–b illustrate the phase difference in the collected signal as a function of collection lens segment.

Referring now to FIG. 3, a sample phase angle difference between segments A, B and C of receiver lens 32 is illustrated. As is apparent, each detector produces an electronic signal that is similar in amplitude, and substantially identical in Doppler frequency, but shifted in phase. With the 3 detector embodiment disclosed detectors 54 and 66 provide maximum sensitivity, while detector 64 insures that the phase angle between detectors 54 and 66 is not greater than 360 degrees. Thus, a logic test is provided in order to preclude the inadvertent measurement of phase differences over more than one fringe and thereby introduce error. Accordingly, the space in between the fringes of the scattered signal may be measured unambiguously. The three detectors 54, 64 and 66 are also used to extend the particle size range capability of the present invention. Using the detector arrangement illustrated in FIGS. 2a and 2b, the phase angle $\phi_{54,66}$ (phase angle between detector output 54 and 66) will be three times as large as the phase angle $\phi_{54,64}$. Thus, angle $\phi_{54,66}$ will provide greater sizing sensitivity for small particles, droplets or the like while $\phi_{54,64}$ permits the measurement of much larger particles. It has been found that the present detector configuration extends the measurement range by a factor of three. However, it will be noted that many additional detector combinations are possible for use with the present invention for providing a variety of sensitivities and ranges.

The theory describing the formation of the reflected and/or refracted fringe pattern generated by a particle, droplet, bubble or the like passing through interference pattern 28 may be understood using the laws of geometric optics. The use of a geometric optic analysis is applicable where the scattering parameter $\alpha = \pi d/\lambda > 10$.

where d is the particle, droplet, bubble, etc., diameter, $\lambda$ is the wavelength of laser 16. In addition, the simplified analysis is applicable if the index of refraction m of the particle, droplet, bubble or the like is sufficiently different (greater or less than) the surrounding medium. Under the appropriate conditions, the light scattered by spherical objects can be described quite accurately. As a result, the present analysis for purposes of this Specification does not require a knowledge of the scattered light intensity. However, the reader is referred to a more detailed analysis to the article by the inventor in *Applied Optics*, Volume 19, No. 3, Feb. 1, 1980.

Figure 4:
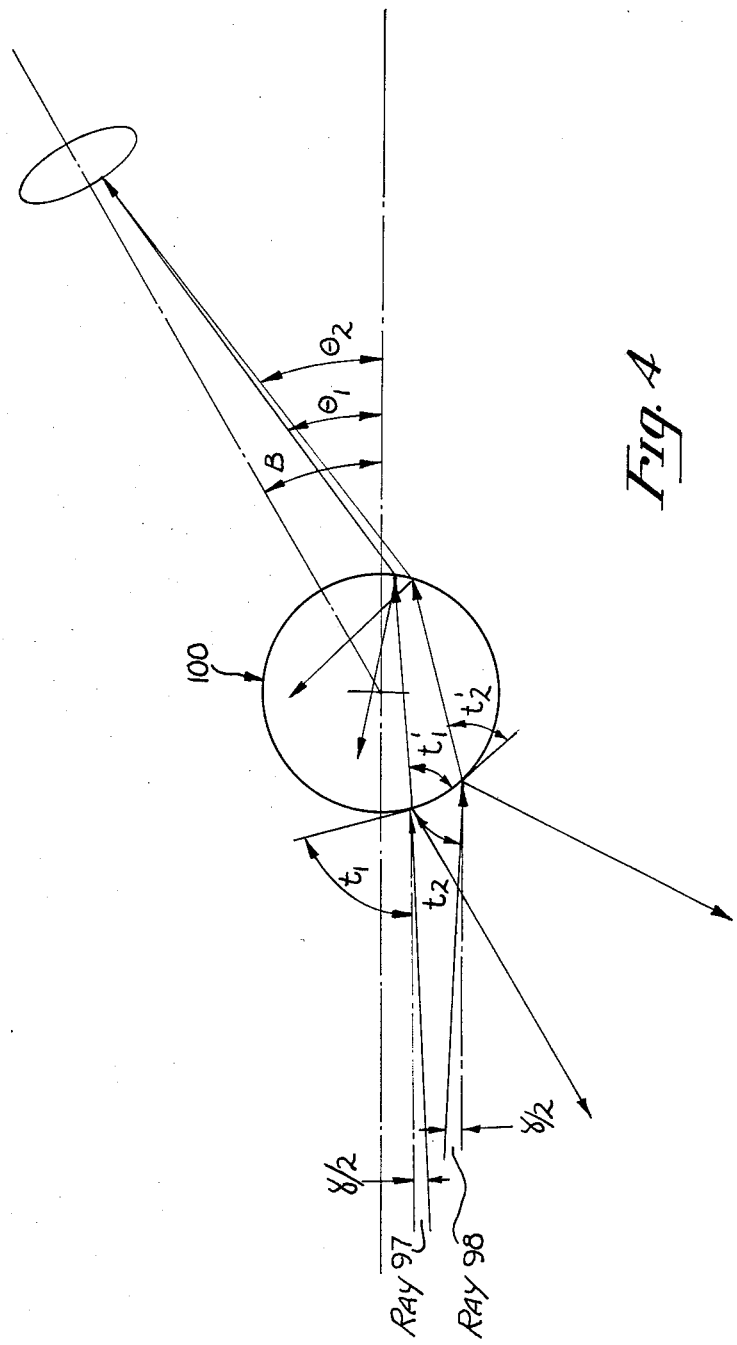

Light scattered by spherical particles greater than the wavelength of light (0.5 micrometers) can be described by the geometric optic theory outlined by Van de Hulst, "Light Scattering By Small Particles", John Wyley and Sons, New York, 1957. As previously discussed, the present invention is based in part on the measurement of the interference pattern formed as a result of two light waves passing through a spherical particle on different paths. Referring now to FIG. 4, a representation of two rays, 97 and 98, are illustrated passing through a droplet 100. As will be apparent, rays 97 and 98 are refracted through the droplet and arrive at a common point on the plane of the collection means optics. The deflection of the light rays 97 and 98 can be described easily using Snell's law. As shown, the two rays 97 and 98 are at an angle $\pm \gamma/2$ relative to horizontal axis. Rays that intersect a common point at the collection optics enter the sphere 100 at specific points on the sphere and angles $t_1$ and $t_2$ are measured from the surface tangents from the sphere 100. A portion of the light is reflected from the first surface of the sphere, and a portion is deflected through the sphere by refraction. The angle of reflection is simply equal to the angle of incidence, whereas the refracted ray is given by Snell's law. Van de Hulst has shown that the angles of the various reflected and refracted rays leaving the sphere can be described using the simple relationship:

$$\Theta = 2(t - pt')$$

where t and t' are the incident and refracted angles shown in FIG. 4, and P is the ray in question leaving the sphere. It will be appreciated that P=0 for the ray reflected at the first surface, and P=1 for the ray passing through the sphere. In addition, P=2 for the ray reflected at the back surface of the sphere 100.

The phase of the light wave passing through the sphere 100 on any discrete path taken at the origin of the sphere is given by the relationship:

$$\delta = 2\alpha(\sin t - M \sin t')$$

Denoting a ray from one of the two beams with subscript 1, and the other by subscript 2. The phase difference may be described as:

$$\Delta = (2\pi d/\lambda)[(\sin t_1 - \sin t_2) - M(\sin t_1' - \sin t_2')]$$

Figure 5:
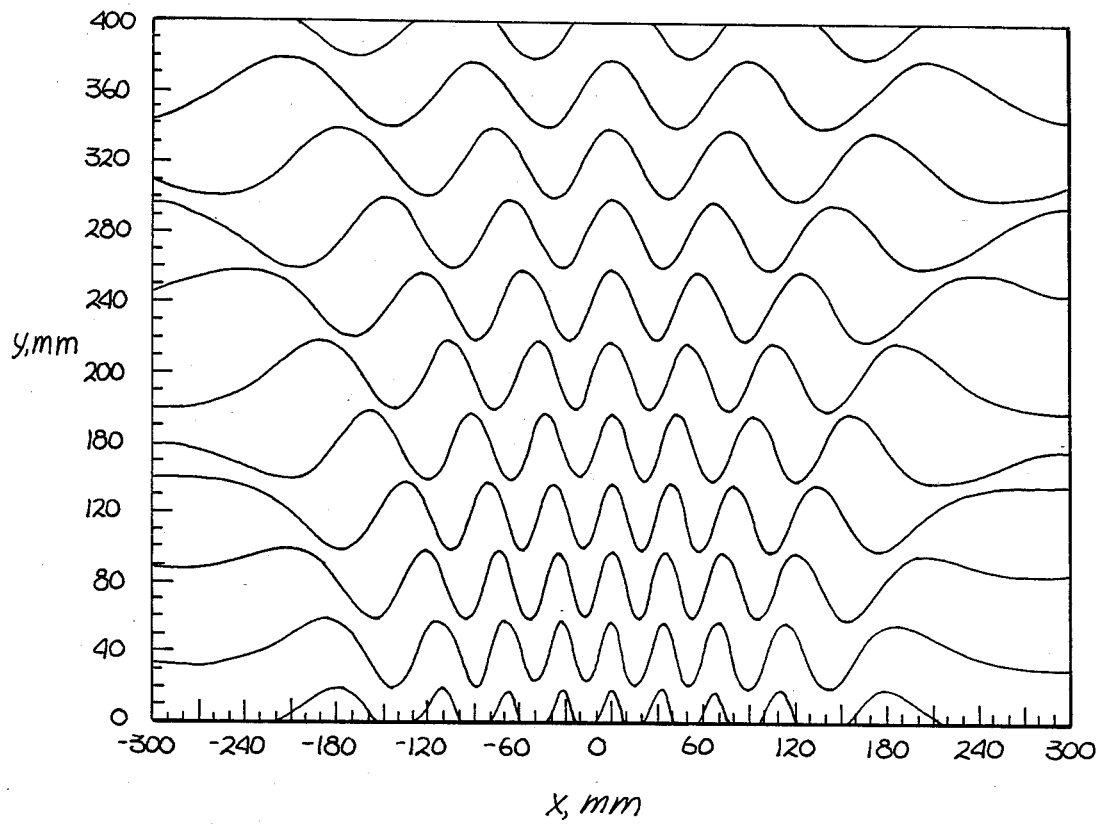
FIG. 5 illustrates a computed sinusoidal interference pattern in accordance with the teachings of the present invention.

The above expression may be used to compute the theoretical description of the actual scattered fringe pattern. Referring now to FIG. 5, there is shown the computed sinusoidal light intensity variation of the scattered fringe pattern. The computed interference fringe pattern is graphed as a function of X-Y position, and a similar pattern may be generated utilizing the above expression for the back scatter fringe pattern.

It has been found that the ratio of droplet size, d, to the light wave length $\lambda$ is a direct multiplier of the angular expression for the phase shift. In addition, it has been found that the index of refraction is also a significant constant in the expression. Moreover, the effect of the incident beam angle $\gamma$ can be appreciated from FIG. 5, since it dictates the paths through sphere 100. For example, a relatively large angle (e.g. 10°) would result in ray paths that have a relatively large phase difference.

It is readily apparent that altering the beam intersection angle $\gamma$ is a straightforward means of setting the spherical particle size range utilizing the teachings of the present invention. A relationship between the beam intersection angle and the spacing of the scattered interference fringe pattern is obtained through the analysis of dual beam light scatter. Since $\theta$ and t are directly related, the angle at which the receiver optics is placed is also included as a factor in the analysis.

It will be noted that the intensity of the radiant flux of the pair of rays considered at each point of the collection means is approximately equal. In fact, it has been found that in some instances the intensity of the scattered light may be used as an additional test of signal ambiguity. In other words, if the phase of the signal was inadvertently measured over more than one cycle, the signal intensity is a useful factor in determining this order of magnitude error.

Figure 3B:
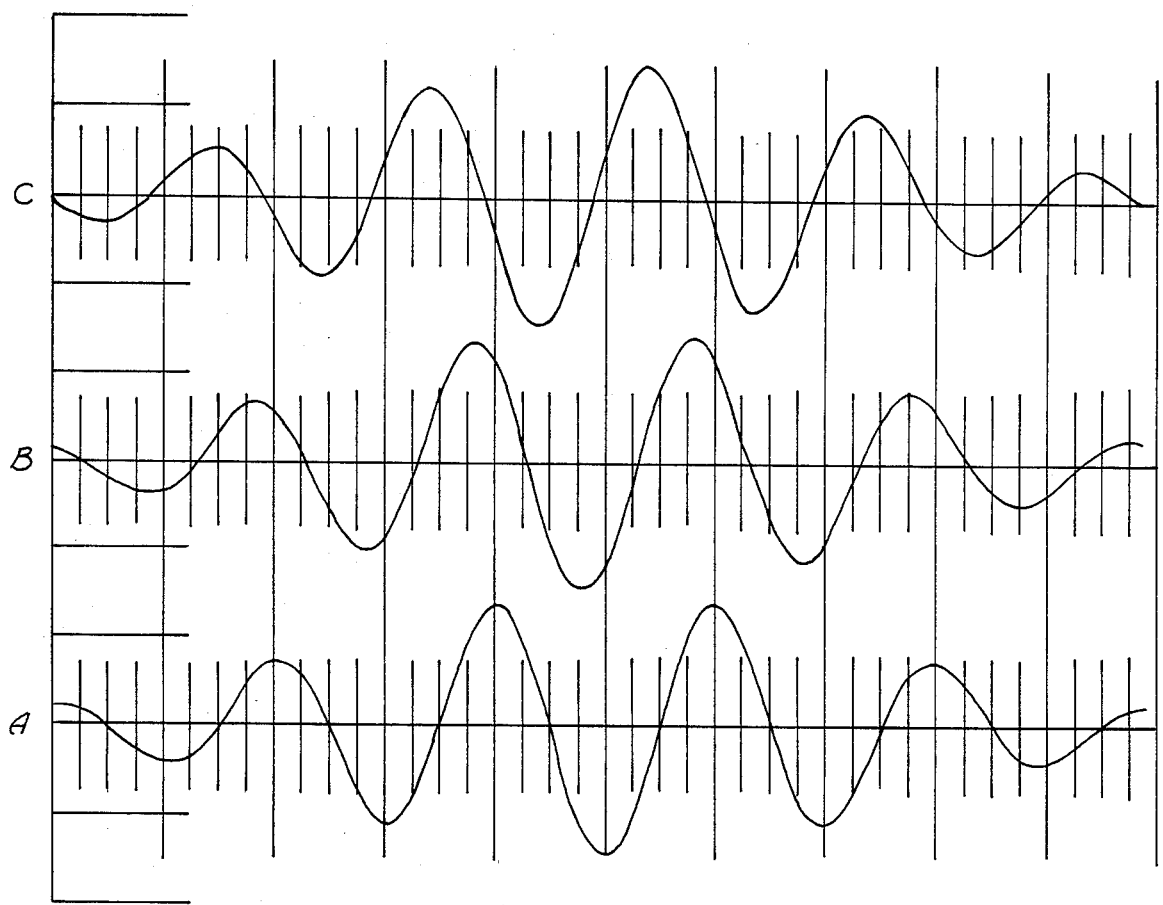

When a spherical particle moves through the fringe pattern 28, the scattered interference fringe pattern which is formed sweeps across the reciver lense 32 at the Doppler frequency. The scattered sinusoidal interference fringe pattern shown in FIGS. 3b and 5, is integrated over each segment, A, B and C, of the receiver collection lens 32, and is transmitted to the respective detectors 54, 64 and 66. An electronic signal is produced by each detector that is proportional to the time varying trace of the integrated light intensity received. Assuming similar gains and detector efficiencies, each signal provided by the photo-detectors 54, 64 and 66 will be identical in frequency but shifted in phase. It has been found, that the interference fringes move in an arc approximately perpendicular to the fringes comprising interference pattern 28. Thus, each segment of the receiver lens collects the same fringe consecutively. Accordingly, the measured Doppler frequency is essentially proportional to the speed of the fringes as they move past each detector. Given the space in between the effective centers of the receiver segments A, B, C, and the fringe speed, the spacing between the fringes may readily be determined.

The electronic signals received from photo-detectors 54, 64 and 66 are preamplified and filtered by low and high pass filtering means. The low pass filtering removes the high frequency noise components, and the high pass filtering removes the pedestal low frequency component of the signals. Of course, care must be taken to ensure that the filtering means does not introduce unknown phase shifts into the signal. Measurement of the Doppler frequency is accomplished using well known techniques of Doppler anemometry. A variety of techniques may be used to measure the phase angle between the signals. As in the case of a Doppler anemometry processor, the electrical signals from photo-detectors 54, 64 and 66 are converted into a square wave of equal frequency. The signals may be electronically multiplied, subtracted, and/or used with logic circuitry to produce a signal with a pulse in proportion to the phase shift. For example, the pulse widths of the phase signal may be averaged over the pulse burst to obtain an averaged phase shift. It will be noted that counters may be used to accurately determine the elapsed time between corresponding points (i.e. zero crossings) of the signals.

Figure 6:
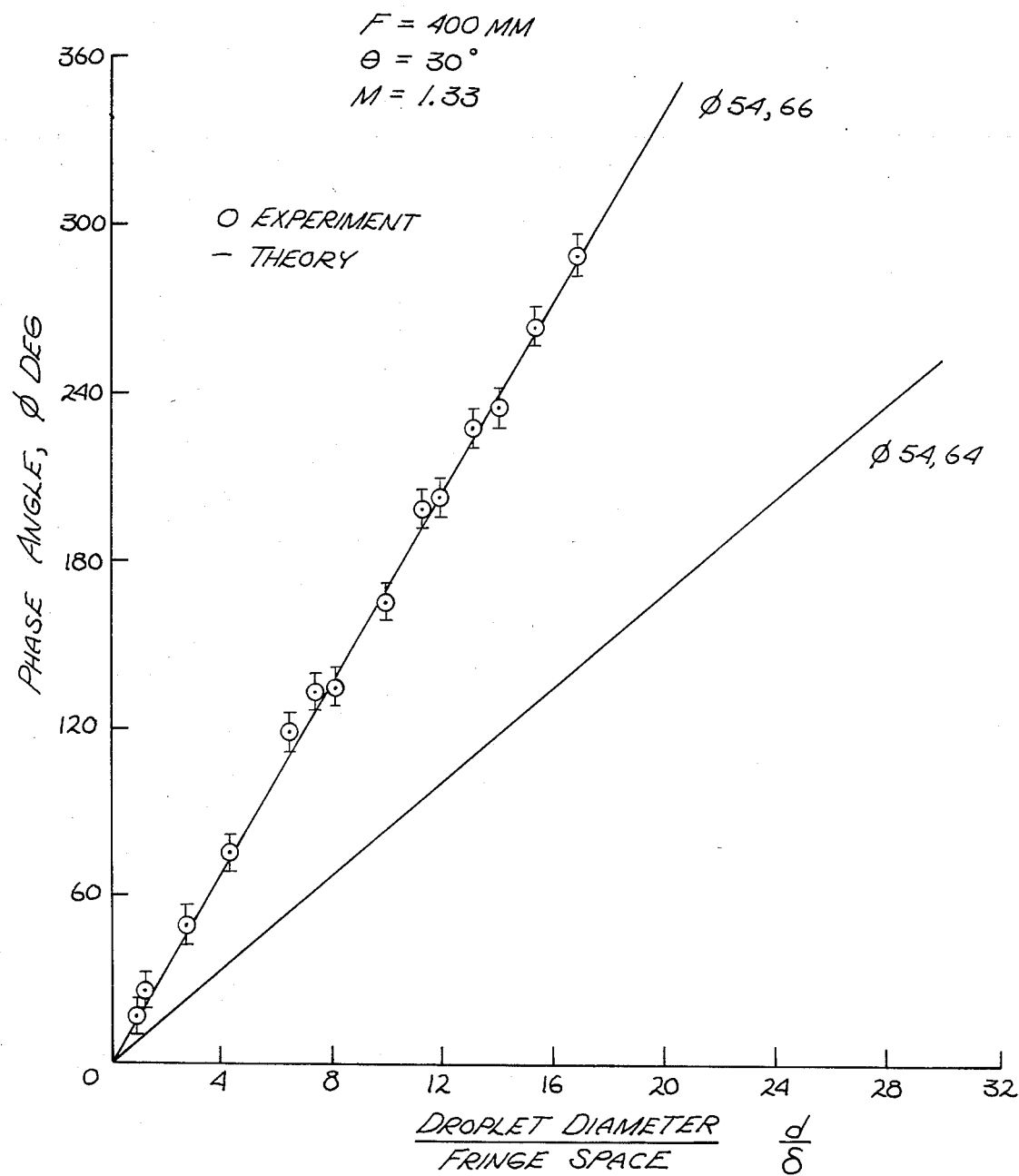
FIG. 6 is a graph illustrating, particle size $d/\delta$ versus phase including a plot of the theoretical and experimental results obtained from the present invention.

Referring now to FIG. 6, a sample output utilizing the teachings of the present invention is disclosed. The FIG. 6 graph includes a plot of both the theoretical as well as experimental results obtained from the present invention. As illustrated, the detected phase angle is linearly related to the spherical particle diameter. Thus, a simple linear relationship may be used with an appropriate adjustable constant, in order to obtain the size of the particle, droplet, bubble, or the like passing through the sample volume. The constant is well determined by instrument parameters. Thus, based on the phase shift, a particle's size may be directly determined. In addition, as previously discussed, the velocity of the particle, droplet, bubble or the like may be determined after high pass filtering of the received signal utilizing well known laser Doppler techniques.

It has been found, that the techniques of the present invention for determining the size of particles, droplets, bubbles or the like permits an increased particle size range not possible in prior art systems. As previously stated, typical prior art signal visibility based methods permit a size range of a decade or less. However, utilizing the teachings of the present invention it has been found that the 3 photo-detector system disclosed permits a size range of over 100 to be measured. Inasmuch as particles having diameters greater than 3 microns scatter light in proportion to their diameter squared, the signal dynamic range of the present invention would theoretically be $10^4$. As a practical matter, a size range of approximately 30 would be accommodated utilizing the present invention's apparatus and techniques at one detector gain setting. However, a significant size range selection may easily be provided utilizing a simple gain control for the photo-detectors 54, 64 and 66.

In addition to the attributes of the present invention disclosed above, it will be appreciated that the direction of motion of the particle droplet, bubble or the like may be obtained utilizing the multiple detector configuration. Typically, a laser Doppler anemometer must use frequency shifting when measuring flows that show flow reversal. The use of multiple photo-detectors permits the direction of the fringe motion, and hence the particle motion to be determined.

For example, consider a detection system that is enabled on the rising edge of the square wave signal and is disabled at the next rising edge of another detector. A left to right moving wave will produce phase shifts substantially as follows:

$$\phi_{54,66}=180°, \phi_{54,64}=60°, \phi_{64,66}=120°$$

where, $\phi$ = phase difference between detectors N and M. (ex. 54 and 66).

If a wave is moving from right to left, the plane shift produced will be approximately:

$$\phi_{54,66}=180°, \phi_{54,64}=240°, \phi_{64,66}=120°$$

when the low numbered detector initiates the measurement.

In the above examples, it is assumed that the possible phase angles $\phi_{54,66} < 360°$. Thus, the flow directions of a particle, droplet, bubble or the like may be determined. In general, the following rules may be used for the detector arrangment illustrated in FIGS. 2(a) and 2(b):

| Particle Direction | Phase |
| --- | --- |
| Right to left | $\phi_{54,66} < \phi_{54,64}$ |
| Left to Right | $\phi_{54,66} > \phi_{54,64}$ |

Thus, an apparatus and method for determining the size and velocity of particles, droplets, bubbles or the like employing laser light scattering has been disclosed. The present invention permits a simple and economical means for determining the velocity and size of particles, droplets, bubbles or the like based on phase changes within the scattered collected signal. The velocity of the particle, droplet, bubble or the like is determined using well known laser Doppler anemometry techniques derived from the high frequency Doppler components in the received scattered signal.

I claim:

1. An apparatus for determining the size of particles, droplets, bubbles or the like, employing laser light scattering, comprising:

laser generation means for providing first and second laser beams;

light directing means for directing said laser beams along an axis and for causing said beams to cross said axis at an angle to establish a sample volume between said pair of beams;

collection means for sensing the scattered interference signal of said pair of laser beams caused by a particle, droplet, bubble or the like passing through said sample volume;

signal phase determining means for determining the phase of said scattered signal sensed by said collection means as said particle, droplet, bubble or the like passes through said sample volume;

sizing means coupled to said signal phase determining means, for determining the size of said particle, droplet, bubble or the like from phase changes in said scattered signal;

whereby the size of a particle, droplet, bubble or the like is determined from the phase of said scattered signal.

2. The apparatus as defined by claim 1 wherein said collection means is disposed off-axis from the axis defined by said crossed beams by a known angle.

3. The apparatus as defined by claim 1 further including at least two detectors, said detectors being coupled to said collection means and said signal phase determining means such that each detector detects a portion of said collected scattered signal.

4. The apparatus as defined by claim 3 wherein said collection means includes a receiver lens.

5. The apparatus as defined by claim 4 wherein said detectors are photo-detectors disposed to detect that portion of said scattered signal passing through segments of said receiver lens.

6. The apparatus as defined by claim 5 wherein said scattered signal comprises sinusoidal interference fringe patterns which sweep across said collection lens segments.

7. The apparatus as defined by claim 6 wherein said collection means further includes directing and focusing means for directing said scattered signal onto said photo-detectors, that portion of said scattered signal passing through each lens segment being directed onto a respective photo-detector.

8. The apparatus as defined by claim 6 further including velocity means for determining the velocity of said particle, droplet, bubble or the like from said scattered signal.

9. The apparatus as defined by claim 8 wherein said velocity means determines the velocity of said particle, droplet, bubble or the like based on the velocity of fringes comprising said scattered signal passing over each of said photo-detectors.

10. The apparatus as defined by claim 6 further including direction determining means for determining the direction of motion of said particle, droplet, bubble or the like based on phase changes in said scattered signal detected by said photo-detectors.

11. An apparatus for determining the direction of motion of a particle, droplet, bubble or the like, employing laser light scattering, comprising:

laser generation means for providing first and second laser beams;

light directing means for directing said laser beams along an axis and for causing said beams to cross said axis at a given angle to establish an interference pattern between said pair of beams;

collection means for sensing the scattered interference signal of said pair of laser beams caused by said particle, droplet, bubble or the like passing through said interference pattern;

signal phase determining means for determining the phase of said scattered signal sensed by said collection means as said particle, droplet, bubble or the like passes through said interference pattern;

direction determining means coupled to said signal phase determining means for determining the direction of motion of said particle, droplet, bubble or the like from phase changes of said scattered signal;

whereby the direction of motion of a particle, droplet, bubble or the like is determined from the phase of said scattered signal.

12. The apparatus as defined by claim 11 wherein said collection means is disposed off-axis from the axis defined by said crossed beams by a known angle.

13. The apparatus as defined by claim 11 further including at least two detectors, said detectors being coupled to said collection means and said signal phase determining means such that each detector detects a portion of said collected scattered signal.

14. The apparatus as defined by claim 13 wherein said collection means includes a receiver lens and said detectors are photo-detectors disposed to detect that portion of said scattered signal passing through segments of said receiver lens.

15. The apparatus as defined by claim 14 wherein said scattered signal comprises sinusoidal interference fringe patterns which sweep across said collection lens segments.

16. The apparatus as defined by claim 15 further including sizing means coupled to said signal phase determining means, for determining the size of said particle, droplet, bubble or the like from phase changes and said scattered signal.

17. The apparatus as defined by claim 16 further including velocity means for determining the velocity of said particle, droplet, bubble or the like from said scattered signal, said velocity means being coupled to said collection means.

18. A method for sizing a particle, droplet, bubble or the like, employing laser light scattering, comprising the steps of:

generating first and second laser beams;

directing said first and second laser beams along an axis, and causing said beams to cross said axis at an angle to establish a sample volume between said pair of laser beams;

sensing the scattered signal of said pair of laser beams caused by a particle, droplet, bubble or the like passing through said sample volume;

determining the phase of said scattered signal as said particle, droplet, bubble or the like passes through said sample volume;

determining the size of said particle, droplet, bubble or the like from phase changes in said scattered signal;

whereby the size of a particle, droplet, bubble or the like is determined from the phase changes of said scattered signal.

19. The method as defined by claim 18 further including the step of determining the velocity of said particle, droplet, bubble or the like from the velocity of fringes comprising said scattered signal.

20. The method as defined by claim 19 further including the step of determining the direction of motion of said particle, droplet, bubble or the like from said phase changes of said scattered signal.

21. The method as defined by claim 20 wherein the phase difference between rays passing through said particle, droplet, bubble or the like may be described by the following relationship:

$$\Delta = (2\pi d/\lambda)[(\sin t_1 - \sin t_2) - M(\sin t_1' - \sin t_2')]$$

where, t and t' are the incident and refracted angles of said rays, $d =$ the diameter of said particle, droplet, bubble or the like, $m =$ index of refraction of said particle, droplet, bubble or the like, and $\lambda =$ wavelength of said rays.

22. A method for determining the direction of motion of a particle, droplet, bubble or the like, employing laser light scattering, comprising the steps of:

generating first and second laser beams;

directing said first and second laser beams along an axis, and causing said beams to cross said axis at an angle to establish a sample volume between said pair of laser beams;

sensing the scattered signal of said pair of laser beams caused by said particle, droplet, bubble or the like passing through said sample volume;

determining the phase of said scattered signal as said particle, droplet, bubble or the like passes through said sample volume;

determining the direction of motion of said particle, droplet, bubble or the like from phase changes in said scattered signal;

whereby the direction of motion of a particle, droplet, bubble or the like passing through said sample volume is determined.

23. The method as defined by claim 22 wherein said sensing step uses at least two detectors, such that each of said detectors senses a portion of said scattered signal.

24. The method as defined by claim 23 wherein said scattered signal comprises sinusoidal interference fringe patterns which sweep across said detectors.

25. The method as defined by claim 24 further including the step of determining the size of droplet, bubble or the like from phase changes in said scattered signal.

26. The method as defined by claim 25 further including the step of determining the velocity of said particle, droplet, bubble or the like from the velocity of fringes comprising said scattered signal.

* * * * *